United States Patent [19]

Udaka et al.

[11] Patent Number: 4,560,748

[45] Date of Patent: Dec. 24, 1985

[54] STREPTOTHRICIN-GROUP COMPOUNDS

[75] Inventors: Shigezo Udaka, Nagoya; Shigeyoshi Miyashiro, Yokohama; Kazuo Hirayama, Tokyo; Toshihiko Ando, Kawasaki; Asao Murai, Tokyo; Tsuyoshi Shiio, Kamakura; Takao Kida, Yokosuka; Hiroshiro Shibai, Chigasaki, all of Japan

[73] Assignee: Ajinomoto Company Incorporated, Tokyo, Japan

[21] Appl. No.: 500,908

[22] Filed: Jun. 3, 1983

[30] Foreign Application Priority Data

Jun. 7, 1982 [JP] Japan ................................. 57-97406

[51] Int. Cl.$^4$ ............................................. C07H 17/00
[52] U.S. Cl. ........................................ 536/24; 514/43; 514/45; 260/112.5 R
[58] Field of Search ................................ 424/180, 181; 260/112.5 R; 536/24; 514/43, 45

[56] References Cited

U.S. PATENT DOCUMENTS 2,474,758   6/1949   Peck ........................................ 536/24

OTHER PUBLICATIONS

Sawada et al., Chemical Modification of Streptothricin-Group Antibiotics, III, Partial N-Acetylation of Racemomycins . . . , Chem. Abs. 81: 20771c (1974).
Sawada et al., Chemical Modification of Streptothricin-Group Antibiotics, IV, Preparation of B-(N-Acetyl) Racemomycin a Derivative . . . , Chem. Abs. 81: 20772d (1974).
Waksman et al., Streptothricin, A New Selective Bacteriostatic and Bactericidal Agent . . . , Chem. Abstracts 36: 3213-8 (1942).
Carter et al., Streptothricin, I, Preparation, Properties and Hydrolysis Products, J. Am. Chem. Soc., 76: 566-569 (1954).

Primary Examiner—Delbert R. Phillips
Assistant Examiner—Charles H. Thieman
Attorney, Agent, or Firm—Oblon, Fisher, Spivak, McClelland & Maier

[57] ABSTRACT

A streptothricin-group compound having the formula:

in which R represents $$-COCH_2CHCH_2CH_2CH_2NHCOCH_2CHCH_2CH_2CH_2NH_2 \text{ or}$$
$$\phantom{-COCH_2C}|\phantom{HCH_2CH_2CH_2NHCOCH_2C}|$$
$$\phantom{-COCH_2}NHCOCH_3\phantom{CH_2CH_2CH_2NHCOCH_2}NH_2$$

$$-COCH_2CHCH_2CH_2CH_2NHCOCH_2CHCH_2-$$
$$\phantom{-COCH_2C}|\phantom{HCH_2CH_2CH_2NHCOCH_2C}|$$
$$\phantom{-COCH_2}NHCOCH_3\phantom{CH_2CH_2CH_2NHCOCH_2}NH_2$$

$$-CH_2CH_2NHCOCH_2CHCH_2CH_2CH_2NH_2$$
$$\phantom{-CH_2CH_2NHCOCH_2C}|$$
$$\phantom{-CH_2CH_2NHCOCH_2}NH_2$$

is disclosed along with methods for producing this compound and a microorganism useful in its production.

1 Claim, 6 Drawing Figures

STREPTOTHRICIN-GROUP COMPOUNDS

BACKGROUND OF THE INVENTION

1. Field of the Invention

The present invention relates to new streptothricin-group compounds, AN-201(I) and AN-201(II), which have antimicrobial and antitumor activities.

2. Description of the Prior Art

Various streptothricin-group compounds produced by Actinomycetes have been known to exhibit antimicrobial activity. However, most of the known streptothricin-group compounds are not of commercial importance because of their toxic properties.

Waksman, S. A. & H. B. Woodruff: Streptothricin, a new selective bacteriostatic and bactericidal agent particulary against gram-negative bacteria. *Proc. Soc. Exptl. Biol. Med.* 49: 207–209, 1942.

Van Tamelen, E. E.; J. R. Dyer, H. A. Whaley, H. E. Carter & G. G. Whitfield, Jr.: Constitution of the streptolin-streptothricin group of Streptomyces antibiotics. *J. Am. Chem. Soc.* 83: 4295–4296, 1961.

Reshetov, P. D. & A. S. Khokhlov: Research of streptothricins by ion-exchange chromatography. *Antibiotiki* 9: 197–201, 1964.

Khokhlov, A. S. & K. I. Shutova: Chemical structure of streptothricins. *J. Antibiotics* 25: 501–508, 1972.

Sawada, Y., H. Sakamoto & H. Taniyama: Studies on chemical modification of streptothricin antibiotics. III. Partial N-acetylation of racemomycins and their biological activity. *Yakugaku zasshi* 94: 176–180, 1974.

Sawada, Y. & H. Taniyama: Studies on chemical modification of streptothricin-group antibiotics IV. Preparation of β-N-acetyl-racemomycin A derivative and its antimicrobial activity. *Yakugaku zasshi* 94: 264–266, 1974.

On the other hand, antitumor compounds are still eagerly awaited, especially antimumor compounds active against solid tumors.

A need, therefore, continues to exist for new substances which exhibit excellent antimicrobial and antitumor activity while also exhibiting substantially reduced toxicity.

SUMMARY OF THE INVENTION

Accordingly, one object of the present invention is to provide compounds which exhibit excellent antimicrobial and antitumor activity with low toxity.

Briefly, this object and other objects of the present invention as hereinafter will become more readily apparent can be attained by new streptothricin-group antibiotics, AN-201(I) and (II) which exhibits antimicrobial and antitumor activities.

DETAILED DESCRIPTION OF THE PREFERRED EMBODIMENTS

Figure 1:
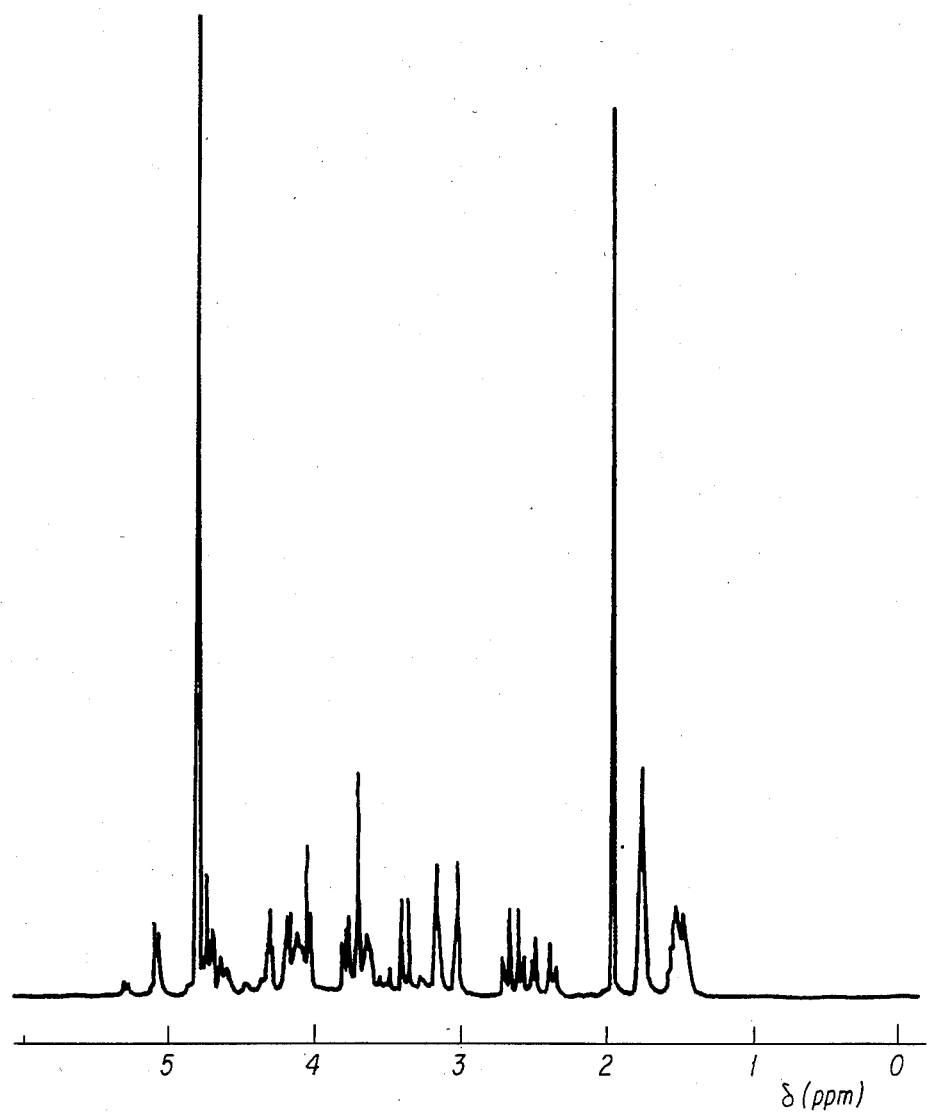
FIG. 1 shows an H-NMR spectrum of AN-201(I).
FIG. II shows an H-NMR spectrum of AN-201(II).
FIG. III shows a $^{13}$C-NMR spectrum of AN-201(I).
FIG. IV shows a $^{13}$C-NMR spectrum of AN-201(II).
FIG. V shows an infrared spectrum of AN-201(I).
FIG. VI shows an infrared spectrum of AN-201(II).
Figure 2:
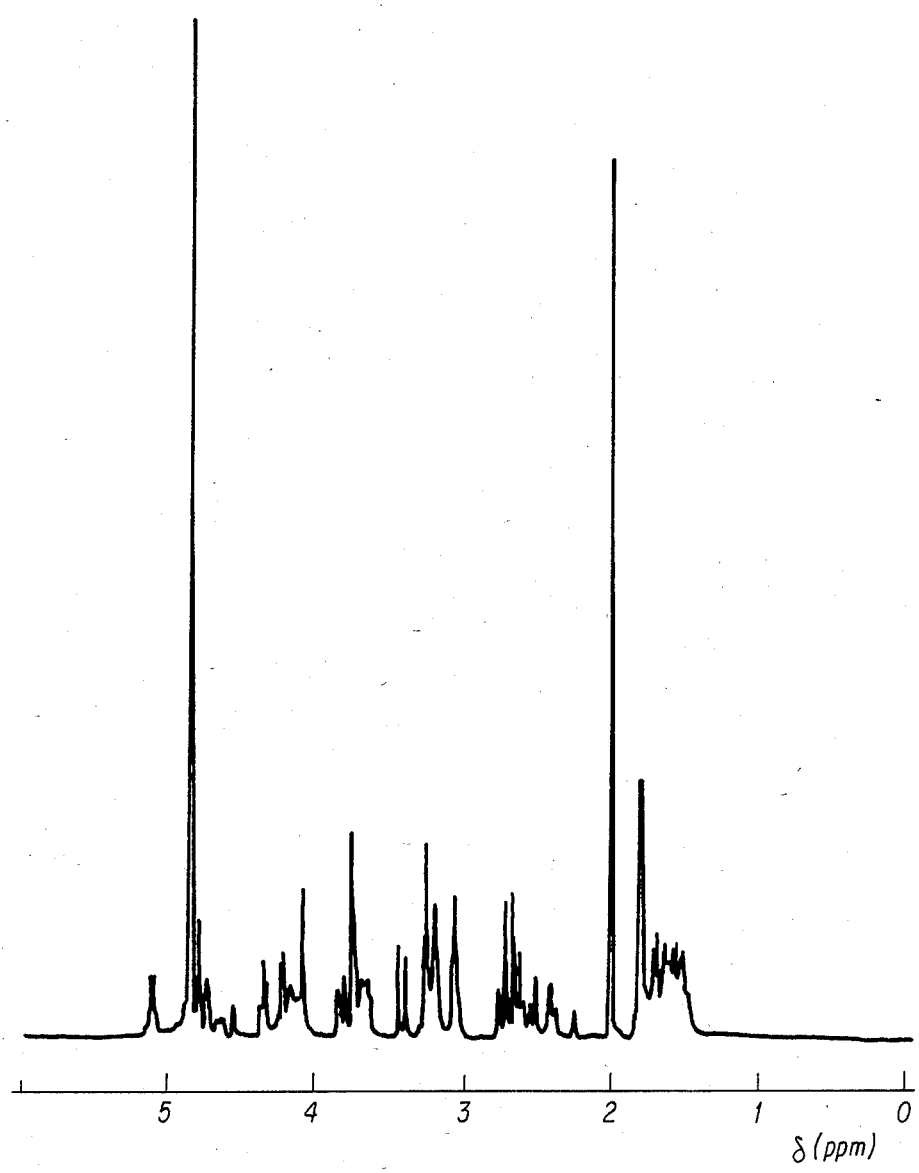
Figure 3:
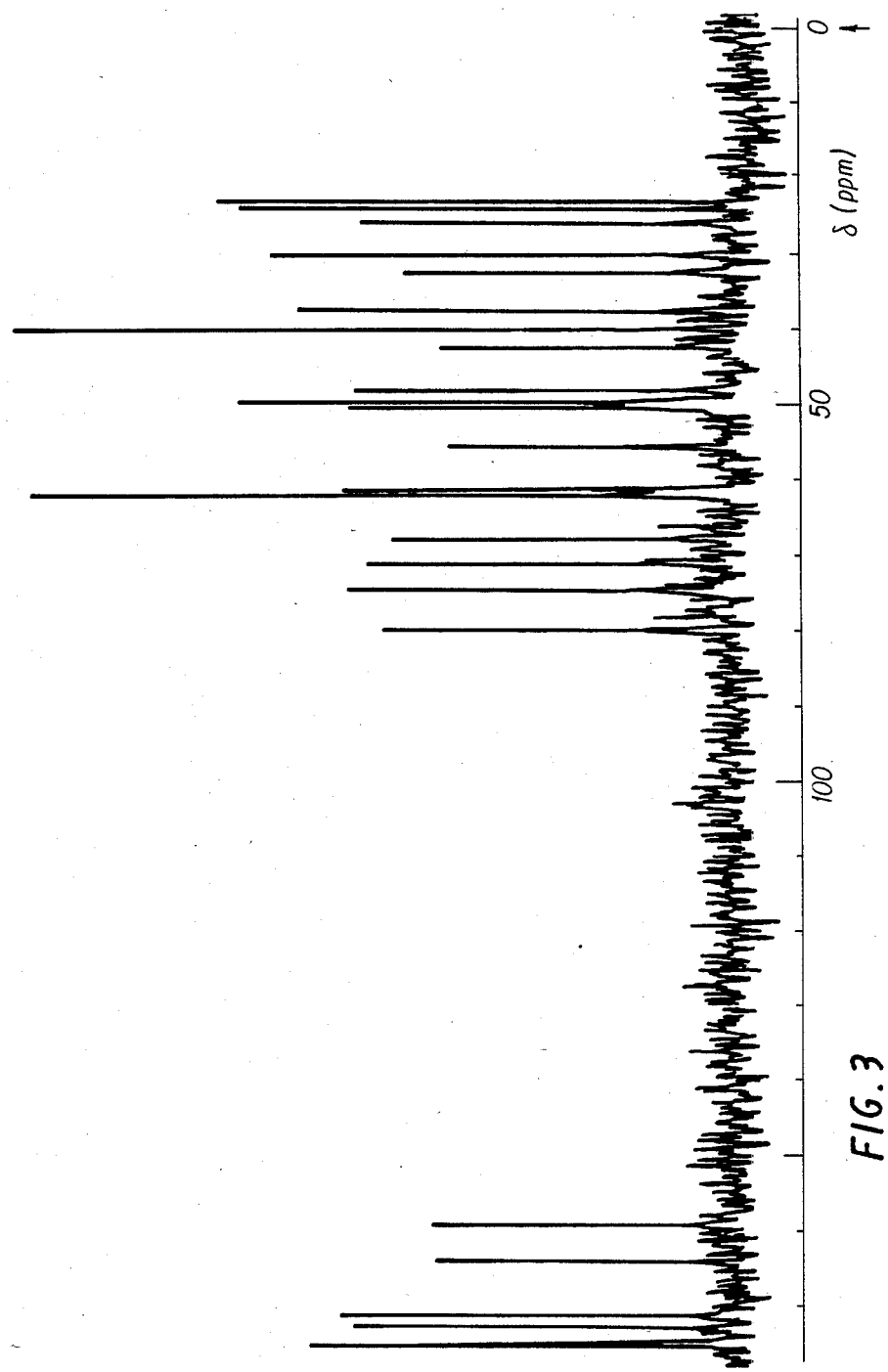
Figure 4:
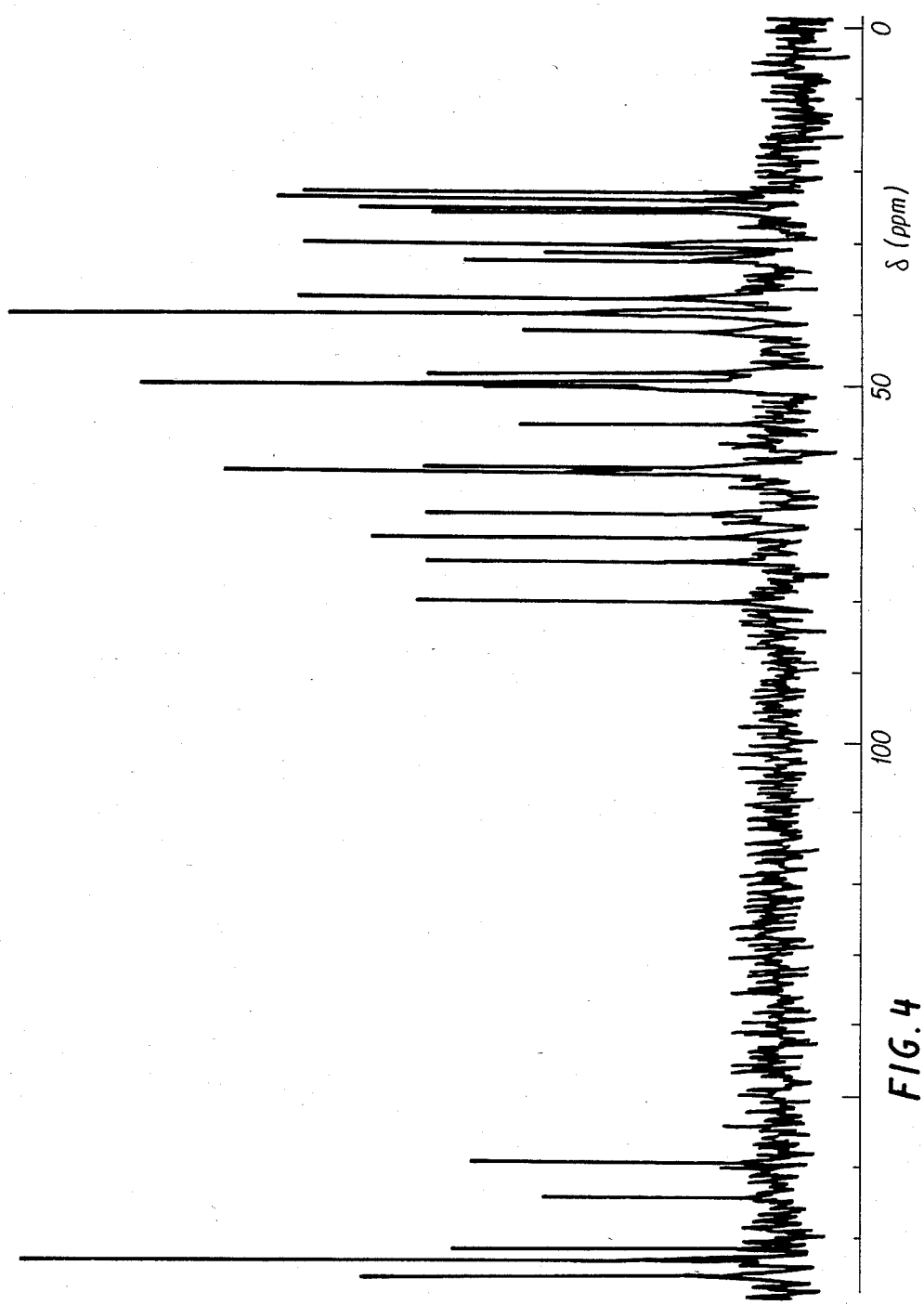
Figure 5:
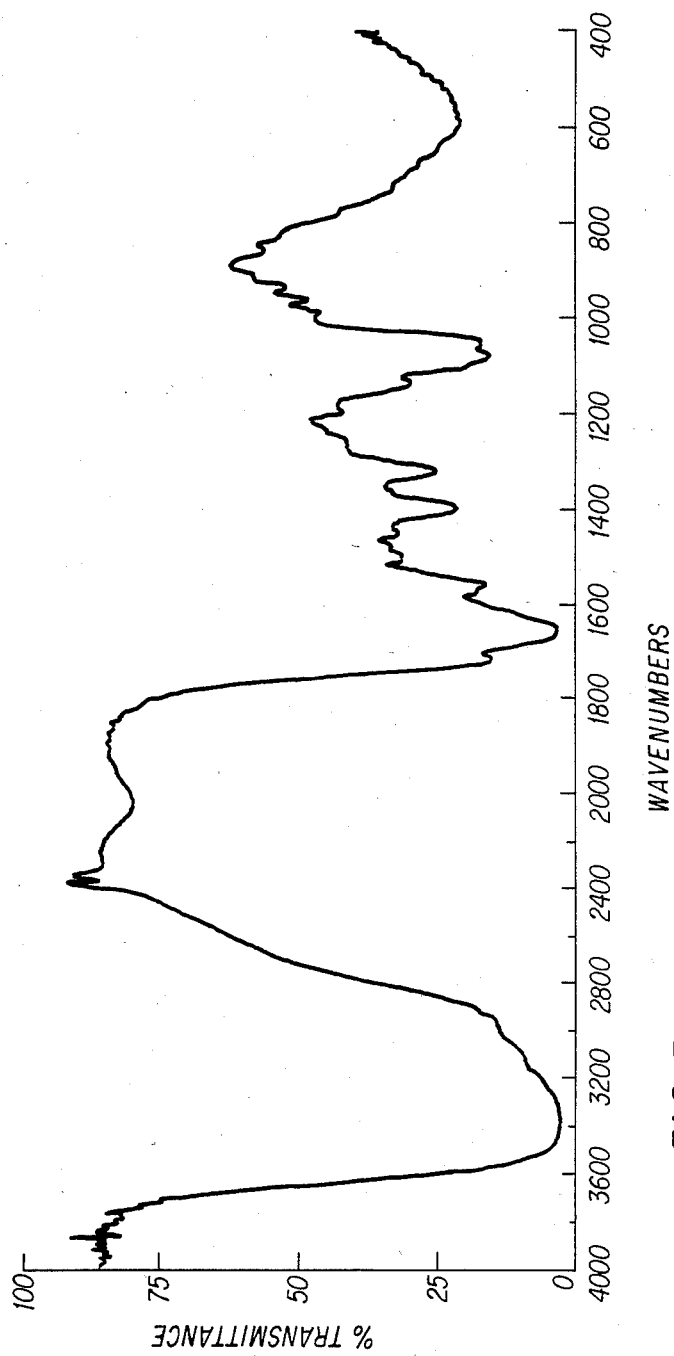
Figure 6:
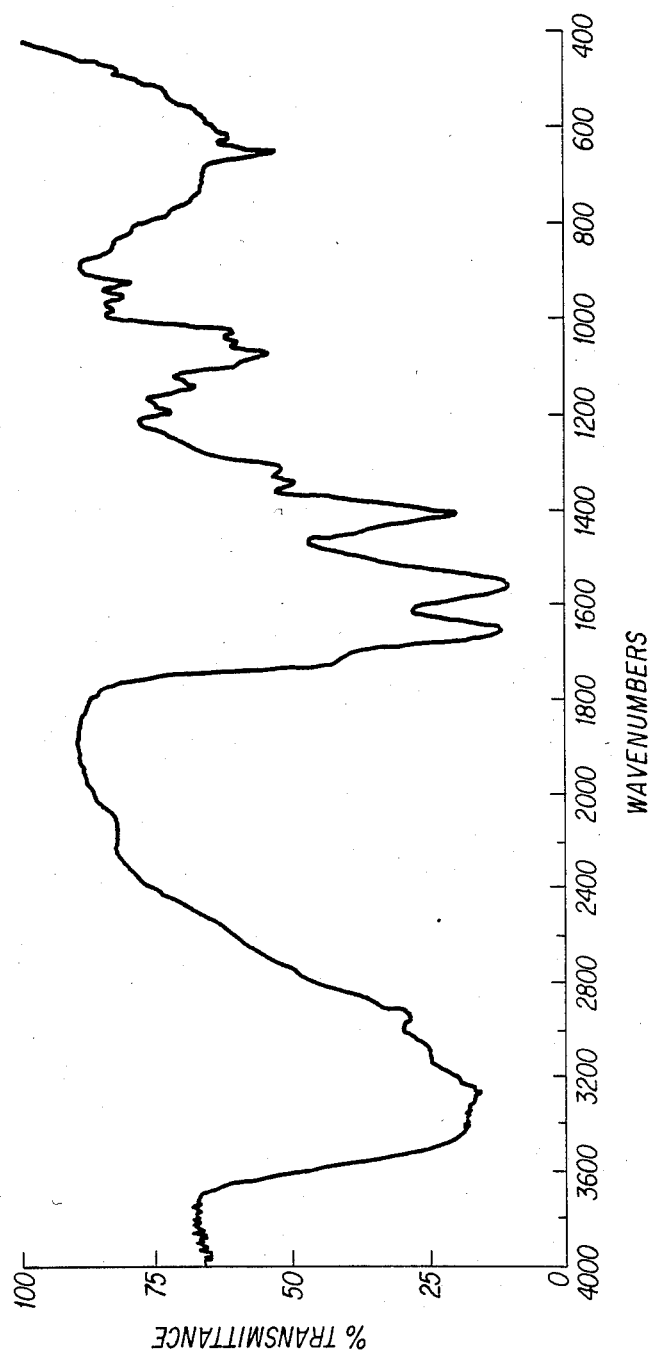

New streptothricin-group compounds AN-201(I) and (II) which exhibits antimicrobial and antitumor activity with extremely low toxicity have been found in, and obtained from, a culture broth of a microorganism belonging to the genus Streptomyces.

AN-201(I) and (II) obtained from a culture broth and purified by a series of conventional purification techniques have the following chemical and physical characteristics:

AN-201(I)

(a) Chemical structure

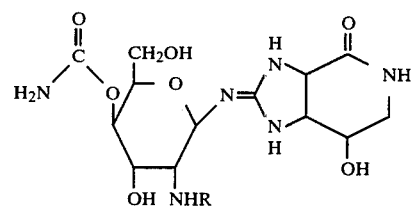

R represents

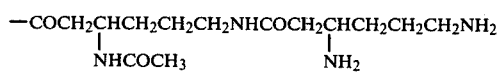

(b) Ninhydrin reaction: Positive
(c) Molecular weight: 672 (FAB-MS)
(d) 'H-NMR (in D$_2$O) spectrum: as shown FIG. I
(e) $^{13}$C-NMR (in D$_2$O) spectrum: as shown in FIG. II
(f) Infrared spectrum: as shown in FIG. V
(g) Antimicrobial activity: positive against *Bacillus subtilis* ATCC 6633, *Sarchina lutea* ATCC 9341 and *Streptococcus aureus* FDA 209P.
(h) Antitumor activity:
(1) positive against LEWIS lung carcinoma in mouse.
(2) cytotoxic selectively against 3T3 cell transformed with SV-40

AN-201(II)

(a) Chemical structure

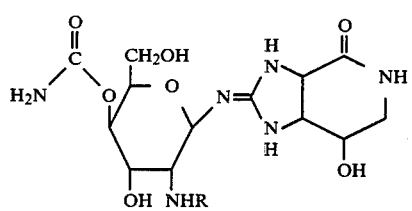

R represents

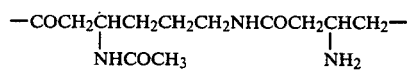

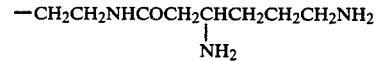

(b) Ninhydrin reaction: positive
(c) Molecular weight: 800 (FAB-MS)
'H-NMR (in D$_2$O) Spectrum: as shown in FIG. II
(e) $^{13}$C-NMR (in D$_2$O) Spectrum: as shown FIG. IV
(f) Infrared Spectrum: as shown in FIG. VI
(g) Antimicrobial activity: positive against *Bacillus subtilis* ATCC 6633, *Sarchina lutea* ATCC 9341 and *Streptococcus aureus* FDA 209P.

(h) Antitumor activity:
(1) positive against LEWIS lung carcinoma in mouse.
(2) cytotoxic selectively against 3T3 cell transformed with SV-40

AN-201(I) and (II) differ from the known streptothricin-group compounds in the points that AN-201(I) and (II) contain in their molecules both β-lysine and N$^\beta$-acetyl-lysine.

Of the known agents, bleomycin (GLM), which is reported to have a notable antitumor activity against LEWIS lung carcinoma in mouse and to exhibit a very high chemotherapeutic coefficient, has been commercialized as a cancer chemotherapeutic agent for human cancer. Compared with BLM, AN-201(I) and (II) were more strongly and selectively cytotoxic to 3T3 cell transformed with SV-40. Moreover, AN-201(I) and (II) showed a greater life prolongation effects for mouse suffered from LEWIS lung carcinoma than BLM. Therefore AN-201(I) and (II) are expected to be more useful as an anticancer agent for human cancer.

In order to produce AN-201(I) and (II), microorganisms of the genus Streptomyces (such as *Streptomyces nojiriensis*)capable of producing AN-201(I) and/or (II) are cultured and in a culture medium, and AN-201(I) and/or (II) accumulated in a culture medium, and AN-201(I) and/or AN-201(II) accumulated in the culture medium are recovered.

The specimen of microorganisms capable of producing AN-201(I) and/or (II) is *Streptomyces nojiriensis* AJ9417 FERM-BP287(FERM-P 5488). In order to culture the microorganisms, conventional media are used and contain a carbon source, a nitrogen source and inorganic ions. Cultivation is conducted by conventional manner under an aerobic condition, preferably adjusting to a pH within the range from pH 4 to pH 9 and the temperature ranging from 20° C. to 35° C.

AN-201(I) and/or (II) can be separated from the resulting culture broth and purified by a series of entirely conventional purifying techniques such as by ion-exchange chromatography using cationic ion-exchange resin or CM-cellulose, solubility difference to solvent, gel filtration using "HP-20", "Bio-Gel P-2" or "Sephadex G-15", and paper electrophoresis.

The strain identified above by the indicated FERM-BP number was originally deposited on Apr. 16, 1980 as FERM-P 5488 at the Fermentation Research Institute, Agency of Industrial Science and Technology, Ministry of International Trade and Industry (FR1) 1-3, Higashi 1-chrome, Yatabe-machi, Tsukuba-gun, Ibaraki-ken 305, JAPAN. This deposit was converted to a deposit under the Budapest Treaty in May, 1983 with FRI which has acquired the status of an International Depository Authority as of May 1, 1981.

The taxonomic characteristics of *Streptomyces nojiriensis* AJ9417 was investigated with the methods described by SHIRLING and GOTTLIED (Intern. J. Syst. Bacteriol., 16, 313, 1966). Classification was carried out in accordance with "Bergey's manual of determinative bacteriology", 8th edition.

The characteristics of AJ9417 are described below:
(a) Morphological observation
The chain of mature spores consists of more than 10 spores and forms loops and occasional spirals. The spores are oval and 0.3~0.5×0.7~0.9 μm. Surfaces of sporulated colonies are smooth.
(b) Culture characteristics

| Medium | |
| --- | --- |
| Sucrose-nitrate agar | (1) Growth: Poor |
| | (2) Aerial mass color: None |
| | (3) Reverse side color: Grayish pink or moderate yellowish pink. |
| | (4) Soluble pigment: None |
| Glucose-asparagine agar | (1) Growth: Moderate |
| | (2) Aerial mass color: Gray |
| | (3) Reverse side color: Grayish pink or light purplish-gray |
| | (4) Soluble pigment: None |
| Glycerin-asparagine agar | (1) Growth: Moderate |
| | (2) Aerial mass color: Grayish white |
| | (3) Reverse side color: Grayish yellow or light purplish gray. |
| | (4) Soluble pigment: None |
| Starch agar | (1) Growth: Moderate |
| | (2) Aerial mass color: Grayish white |
| | (3) Reverse side color: Grayish pink or light yellowish brown. |
| | (4) Soluble pigment: None |
| Tyrosine agar | (1) Growth: Moderate |
| | (2) Aerial mass color: None |
| | (3) Reverse side color: Grayish yellow |
| | (4) Soluble pigment: None |
| Nutrient agar | (1) Growth: Poor |
| | (2) Aerial mass color: None |
| | (3) Reverse side color: Moderate yellowish brown |
| | (4) Soluble pigment: Melanoid pigment |
| Yeast-malt extract agar | (1) Growth: Abundant |
| | (2) Aerial mass color: Light purplish gray |
| | (3) Reverse side color: Cinnamon or moderate orange |
| | (4) Soluble pigment: None |
| Oatmeal agar | (1) Growth: Abundant |
| | (2) Aerial mass color: Light purplish gray |
| | (3) Reverse side color: Moderate yellowish pink |
| | (4) Soluble pigment: None |

(c) Physiological characteristics
Temperature range for growth is from 15° to 39° C. and optimum temperature is from 30° to 37° C. Starch hydrolysis and milk coagulation are negative. Gelatin liquefaction and milk peptonization are positive. Melanin production is negative on tyrosine agar and positive on peptone-yeast extract-iron agar. D-glucose and salicin are utilized, but L-arabinose, sucrose, L-rhamnose, raffinose, D-xylose, D-fructose, inositol, D-mannitol and D-gelactose are not utilized.

(d) Basic amino acid of cell wall
Whole cell hydrolysates: L-diaminopimelic acid is found in whole cell hydrolysate.

AN-201(I) and (II) can be assayed by determining anti-microbial activity to *E. coli* MP-2 (FERM-P 5432) (Agric. Biol. Chem., 43, 371, (1979)), which has permeability for high molecular compounds.

EXAMPLE (1) Production of AN-201(I) and (II)
A culture medium containing, per liter, 30 g glucose, 5.0 g peptone, 10 g bouillon, 5.0 g NaCl and 2.0 g CaCl$_2$.2H$_2$O was prepared, the pH of the medium was adjusted to pH 7.2, and 100 ml batches of the medium were placed in 500 ml flasks and heated at 120° C. for 15 minutes to sterilize. An one milliliterinoculum of *Strep-* tomyces nojiriensis AJ9417 was transferred into the medium, which was thereafter held at 30° C. for 24 hours.

Ten liters of the culture medium mentioned above was placed in a 20 l-stainless-jar-fermenter, sterilized by heat, inoculated with 200 ml of the culture liquid mentioned above and held at 28° C. for 24 hours agitating at 300 rpm while aerating in the rate of 5 l/minutes. Two hundred liter of the culture medium mentioned above was placed in a 300 l stainless-tank, sterilized by heat, and inoculated with the 10 l of the culture broth obtained above, and held at 29° C. for 24 hours agitating at 180 rpm while aerating at 200 l/min.

From 180 l of the resulting culture broth, mycelia were removed by filtration, and the filtrate having 180 units/ml of antimicrobial activity against E. coli MP-2 was obtained. The supernatant was adjusted to pH 8.4 with NaOH, and applied to 10 l of "IRC-50" (H+) ion exchange resin column, which was thereafter washed with water. Then the elution of AN-201 was made with 0.2 NHCl. Eluate containing AN-201 (60 l) was collected, adjusted to pH 5.0 with 2N HCl, subjected to evaporation to 6 l, and added with methanol. Precipitate formed was removed and to the supernatant was added 1 l of methanol and further 5 l of acetone. Precipitate formed by stirring at 5° C. for 30 minutes was separated and dried to obtain 10 g of pale yellow powder.

The powder was dissolved in 0.5M pyridine-acetate buffer of pH 4.8, and the solution was charged on CM-sephadex C-50 previously equilibrated with 0.5M pyridine-acetate buffer of pH 4.8. Elution was carried out by changing the pyridine-acetate buffer used from 0.5M to 4.0M, obtaining 200 mg of AN-201(I) and 200 mg of AN-201(II). Relative mobilities of AN-201(I) and (II) were 0.86 and 0.90, respectively, as compared to 1.00 of streptothricin F, when the AN-201(I) and AN-201(II) samples were subjected to paper electropholesis, which was carried out for 1.5 hours at 30 V/cm using Toyo filter paper No. 50 a solvent of pyridine-acetate-$H_2O$ (10:100:890).

Each sample of AN-201(I) and (II) gave a single spot by ninhydrin color development on the paper electrophoresis.

(2) Characteristics of AN-201(I) and (II)

The chemical structures for AN-201(I) and (II) were determined as to the samples obtained above by FD-MS, FAB-MS, NMR and amino acid analysis. AN-201(I) and (II) have the aforementioned chemical, and physical characteristics.

(3) Physiological properties of AN-201(I) and (II)

(a) Antimicrobial activities:

Two ml portions of $M_3$-Medium (Bactoantibiotic Medium—Difico, 1.75%, pH 7.2) were placed into test tubes and heated at 120° C. for 10 minutes. Each test strain in Table 1 was inoculated into a batch of culture medium, and the inoculated batches were cultured with shaking at 30° C. for 20 hours to obtain seed culture broths. A 0.05 ml sample of each culture broth was inoculated into 20 ml of $M_3$-Medium containing AN-202(I) or (II). The inoculates were cultured at 37° C. for 20 hours with shaking. Thereafter, the optical density of each resultant culture broth at 660 nm was determined, and the minimum inhibition concentration (MIC) of each broth was calculated, and is shown in Table 1.

TABLE 1

| Test Strain | MIC ($\mu$g/ml) | |
|---|---|---|
| | AN-201(I) | AN-201(II) |
| Escherichia coli K-12 ATCC 10798 | >50 | >50 |
| Escherichia coli MP-2 | 20 | 4.0 |
| Bacillus subtilis ATCC 6633 | 2.7 | 1.5 |
| Sarcina lutia ATCC 93412 | 5.0 | 5.0 |
| Pseudomonas aeruginosa ATCC 10145 | >50 | >50 |
| Staphylococcus aureus FDA 209 P | 2.0 | 2.0 |

(b) Activity against SV 3T3 (transformed strain with virus):

MEM Uldecco powder (DAI-NIPPON SEIYAKU) (13.45 g) was dissolved in 1 l of distilled water and 2 ml of 7.5% $NaHCO_3$ solution was added to the solution. Then the solution was filtered through a Millipore filter (pore size: 0.22$\mu$) and supplemented with 100 ml of germ-free blood serum. Into a micro test plate (Falcon), 0.15 ml portions of the culture medium thus prepared were placed. Then a 0.05 ml culture sample of previously cultured mouse fibroblast cell 3T3 or mouse fibroblast cell 3T3 transformed with Semian virus-40 (SV 3T3) was inoculated into each portion of the culture medium. Thereafter, the inoculated media were incubated in a $CO_2$ gas incubator (concentration of $CO_2$ gas: 7.0%) at 37° C. for 24 hours. Into the media AN-201(I) or (II) was added to contain 20 $\mu$g/ml, 40 $\mu$g/ml, 50 $\mu$g/ml or 60 $\mu$g/ml, and additional cultivation was carried out for 3 days. Number of injured cell in each medium was counted with an invert microscope using a Thama hematometer. The results are shown in Table 2.

TABLE 2

| Sample added ($\mu$g/ml) | Number of Injured Cell | | | |
|---|---|---|---|---|
| | 3T3 | | SV-3T3 | |
| | AN-201(I) | AN-201(II) | AN-201(I) | AN-201(II) |
| 0 | − | − | − | − |
| 20 | − | − | − | − |
| 40 | − | − | + | + |
| 50 | + | + | +++ | +++ |
| 60 | ++ | ++ | +++ | +++ |

−: none of the cells injured
+: half of the cells injured
++: about ⅔ of the cells injured
+++: almost all of the cells injured Normal cells, 3T3 and SV-40-transformed 3T3 cells, (SV3T3) were cultured in Eagle's minimal essential medium supplemented with 10% calf serum, 5 $\mu$g/ml of cefazoline and 100 $\mu$g/ml of streptomycin at the initial cell concentration of $4 \times 10^4$ cells/2 $cm^2$ for 3T3 and $2 \times 10^4$ cells/2 $cm^2$ for SV3T3 at 37° C. in 7% $CO_2$ incubator. After one day of cultivation old medium was removed from tissue culture plate and various concentrations of drug diluted with new medium were added to the Falcon tissue culture plate. After 2 days of cultivation, the cell density was measured and the value of ED50 was determined. N/T ratio was calculated from ED50 value of normal cell, 3T3, to transformed cell, SV3T3. These results are also shown in Table 3.

TABLE 3

| Antibiotics | ED50 (μg/ml) 33T3(N) | SV3T3(T) | Selective cytotoxic effect (N/T ratio) |
|---|---|---|---|
| AN-201(I) | 55 | 25 | 2.2 |
| AN-201(II) | 50 | 15 | 3.3 |

(c) Effect on L 1210 cell

A 10.28 g sample of RPMI 1640 powder medium (DAI-NIPPON SEIYAKU) was dissolved into 1.0 liter distilled water and 1.0 g $NaHCO_3$ was added to it. Then the solution was filtered through a Millipore filter (pore size: 0.22μ) and supplemented with 100 ml of germ-free blood serum. One ml portions of the culture medium thus prepared were placed into Falcon Multi Well aseptically. Then a 0.05 ml culture sample of mouse leukemia L 1210 cells previously cultured was inoculated into each batch of the culture medium, and a definite amount of purified AN-201(I) or (II) dissolved in the same medium was added simultaneously to the culture medium. Thereafter, the inoculated media were incubated in a $CO_2$ gas incubator (concentration of $CO_2$ gas: 7.0%) at 30° C. After 5 days incubation, the numbers of multiplied cells were counted under a microscope and the relative multiplication numbers obtained are shown in Table 4.

TABLE 4

| Concentration (μg/ml) | Relative multiplication number AN-201(I) | AN-201(II) |
|---|---|---|
| 0 | 100 | 100 |
| 10 | 100 | 100 |
| 20 | 80 | 80 |
| 40 | 30 | 25 |
| 50 | 0 | 0 |
| 60 | 0 | 0 |

(d) Effect on LEWIS lung carcinoma

LEWIS lung carcinoma (1 mm³) was transplanted subcutaneously into $BDF_1$ mice. After 24 hours of the transplantation, AN-201(I), (II) and BLM were intraperitoneally injected daily for 1-10 days. Antitumor activity was indicated with a reduction in tumor size or with a increase in life span. These results are shown in Table 5.

TABLE 5

| Antibiotics | Dose (mg/kg) | Reduction of tumor size (%) | I.L.S. (%) |
|---|---|---|---|
| AN-201(I) | 9 | 45–50 | 114–120 |
| | 18 | 50–65 | 120–125 |
| AN-201(II) | 1 | 50–57 | 101–110 |
| | 3 | 54–60 | 121–130 |
| | 9 | 74–85 | 124–135 |
| BLM | 5 | 52–60 | 100–110 |
| | 10 | 65–80 | 119–124 |

What is claimed is:

1. A streptothricin-group compound having the following formula:

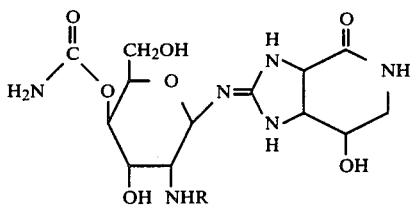

in which R represents

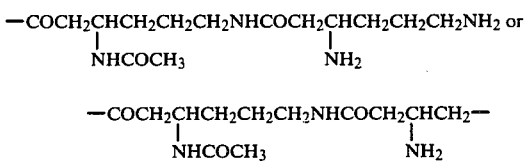

—$CH_2CH_2NHCOCH_2CHCH_2CH_2CH_2NH_2$
         |
         $NH_2$

* * * * *